United States Patent [19]

Schlosberg et al.

[11] 4,256,568

[45] Mar. 17, 1981

[54] REMOVAL OF PHENOLS FROM PHENOL-CONTAINING STREAMS

[75] Inventors: Richard H. Schlosberg, New Providence; Charles G. Scouten, Westfield, both of N.J.

[73] Assignee: Exxon Research & Engineering Co., Florham Park, N.J.

[21] Appl. No.: 95,640

[22] Filed: Nov. 19, 1979

[51] Int. Cl.$^3$ .................... C10G 1/00; C10G 19/08; C07C 37/68; C07C 19/08

[52] U.S. Cl. .................... 208/263; 208/8 R; 568/749; 568/761

[58] Field of Search .................... 260/263; 568/761

[56] References Cited

U.S. PATENT DOCUMENTS

| | | | |
|---|---|---|---|
| 1,819,687 | 8/1931 | Miller | 568/761 |
| 3,617,513 | 11/1971 | Wilson et al. | 208/127 |

FOREIGN PATENT DOCUMENTS

| | | | |
|---|---|---|---|
| 866064 | 8/1978 | Belgium | 208/263 |
| 838900 | 3/1939 | France | 208/263 |
| 494450 | 10/1938 | United Kingdom | 208/263 |

OTHER PUBLICATIONS

Gardner et al., "Magnesium Hydroxide in the Petroleum Industry", Ind. Eng. Chem. 24, 1141–1146 (1932).

*Primary Examiner*—W. J. Shine
*Assistant Examiner*—G. E. Schmitkons
*Attorney, Agent, or Firm*—Henry E. Naylor

[57] ABSTRACT

Process for removing phenols from phenol-containing streams such as coal liquids by contacting the stream with a multivalent metal composition selected from the group consisting of oxides and/or hydroxides of one or more multivalent metals capable of forming a hydroxy metal phenate with the phenols of the stream; separating the hydroxy metal phenate from the treated stream; and heating the hydroxy metal phenate to its decomposition temperature, thereby forming phenols and oxides of the multivalent metal.

18 Claims, No Drawings

REMOVAL OF PHENOLS FROM PHENOL-CONTAINING STREAMS

BACKGROUND OF THE INVENTION

1. Field of the Invention

The present invention relates to the removal of phenols from phenol-containing hydrocarbonaceous streams by use of multivalent metal oxides and/or hydroxides whereupon the resulting hydroxy metal-phenate is pyrolyzed to recover the phenol and an oxide of the multivalent metal.

2. Description of the Prior Art

The presence of phenols in various hydrocarbonaceous streams is troublesome. For example, the presence of phenols in liquids produced from coal causes instability of these liquids over a period of time by increasing the viscosity, the color intensity, and causing separation of resinous materials. Moreover, without extensive hydrotreatment, coal liquids are generally not compatible with petroleum liquids of comparable boiling point. Thus, solids separation caused largely by high concentrations of phenols, leads to severe operability problems for coal/petroleum liquid blends. Also, hydrodesulfurization ahd hydrodenitrogenation of coal liquids are required prior to reforming into motor gasoline. These steps require a very large consumption of hydrogen for phenol-rich coal liquids because of the extensive deoxygenation of phenols to water.

Various methods of removing these troublesome phenols from hydrocarbonaceous streams are taught in the art. For example, it is taught that weakly acid-reacting organic substances such as phenols can be removed from hydrocarbonaceous streams by use of alkali metal or alkaline-earth metal oxides or hydroxides. It is also taught that the phenols react with these oxides or hydroxides resulting in the formation of phenoxide salts which can be easily separated from the purified stream. Further, it is known that certain phenoxide salts, such as calcium phenoxide, can be heated in the presence of carbon dioxide to yield phenols and calcium carbonate.

Another method taught for separating phenols from hydrocarbonaceous streams is to wash the stream with large quantities of water or aqeous caustic solutions such as sodium or potassium hydroxide.

Although such methods are practiced on a commercial scale in various industries, there is still a need to develop a process for removing, from hydrocarbonaceous streams, troublesome phenols and recovering the phenols in a more efficient and inexpensive way.

SUMMARY OF THE INVENTION

In accordance with the present invention phenols are removed from phenol-containing hydrocarbonaceous streams and the phenols are regenerated by a process which comprises: (a) contacting the stream with a multivalent metal composition selected from the group consisting of one or more oxides and/or hydroxides of multivalent metals capable of forming a hydroxy metal phenate with the phenols of the stream, wherein the stream is contacted at a temperature below the decomposition temperature of the hydroxy metal phenate; (b) separating the hydroxy metal phenate from the stream; and (c) heating the hydroxy metal phenate to its decomposition temperature to form phenols and oxides of the multivalent metal.

In a preferred embodiment of the present invention enough multivalent metal composition is employed so that at least 15 wt.% of the total phenols are removed from the stream.

In other preferred embodiments of the present invention the phenol-containing hydrocarbonaceous stream is a coal liquid and the multivalent metal is selected from the group consisting of strontium, barium, calcium and nickel wherein the nickel has a valence of +3.

In still another preferred embodiment of the present invention, the multivalent metal oxides resulting from the decomposition of the hydroxy metal phenate, are hydrolyzed to the corresponding hydroxide and recycled for contacting the feed stream.

DETAILED DESCRIPTION OF THE INVENTION

Phenol-containing hydrocarbonaceous streams which can be treated according to this invention include, but are not limited to, those streams resulting from the processing of coal, petroleum, and those existing as impurities in such parent streams as linear paraffins.

The term phenol-containing hydrocarbonaceous stream means a hydrocarbonaceous stream containing measurable amounts of phenol compounds in which one or more hydroxyl groups are attached to an aromatic ring and where the aromatic ring may also contain a heteroatom (e.g. nitrogen in a pyridine ring). Non-limiting examples of such phenol compounds include phenol itself (also known as benzophenol), the cresols, xylenols, recorcinol, naphthols, 8-hydroxyquinoline and 4-hydroxyquinoline. The phenol-containing hydrocarbonaceous stream, exclusive of the phenol compounds, also contains at least 25 wt.% of compounds containing carbon and hydrogen, though other atoms (e.g. nitrogen, oxygen, sulfur) may also be present.

The present invention is not dependent on the method of producing the phenol-containing hydrocarbonaceous stream. For example, any coal liquid containing phenols can be treated regardless of its method of production. Non-limiting examples of processes for producing coal liquids include pyrolsis, solvent refining, direct hydrogenation with or without a catalyst, catalytic or noncatalytic hydrogenation in the presence of a non-hydrogen donor solvent and catalytic or non-catalytic liquefaction by a hydrogen donor solvent method.

Although not wishing to be limited hereby, one preferred method for obtaining coal-liquids is the Exxon Donor Solvent (EDS) process for the liquefaction of coal and described in U.S. Pat. No. 3,617,513 incorporated herein by reference. Briefly stated, the EDS process involves the formation of a slurry of coal in a hydrogen-donor solvent, such as tetralin, maintained at elevated temperatures of about 260° C. to 370° C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperatures above about 370° C. under a pressure effective to maintain the dispersant slurry substantially in the liquid phase, generally about 350 p.s.i.g. to 3500 p.s.i.g. In this second temperature stage, the dissolved coal particles are well dispersed in the hydrogen-donor solvent and the chance of a hydrogen-donor stabilization of free radicals generated by bond breaking is maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contain phenols, is then distilled and hydrogenated, the gases drawn off, and the bottoms removed for coking and gasification.

In accordance with the present invention, the phenol-containing stream is treated with one or more multivalent metal oxides and/or hydroxides capable of forming a hydroxy metal phenate with the phenols. The stream is contacted at a temperature below the decomposition temperature of the resulting hydroxy metal phenate; generally from about room temperature (20° C.) to the decomposition temperature of the hydroxy metal phenate. For example, when calcium is the multivalent metal of the oxides and/or hydroxides used herein, the decomposition of its resulting hydroxy calcium phenate is about 490° C. The decomposition temperature of any resulting hydroxy metal phenate can be easily determined by one having ordinary skill in the art.

The amount of multivalent metal composition needed in the practice of the invention is dependent on the amount of multivalent metal required to react with a predetermined amount of the phenols in the stream. Although it may be desirable to remove as much of the phenols from the stream as possible, one may only wish to remove a certain minimum amount based on economic considerations.

The concentration of phenols in the hydrocarbonaceous stream can be determined by conventional analytical methods such as non-aqueous titration. The amount of multivalent metal needed to remove a predetermined amount of phenols can be expressed as the mol ratio of metal (in the oxide and/or hydroxide) to phenolic-oxygen (in the feed stream). The preferred mol ratio of metal to phenolic-oxygen needed herein is that ratio which, when the metal oxides and/or hydroxides are contacted with the stream, will assure the removal of at least about 15 wt. % of the phenols from the feed stream at a temperature of about 25° C. for a contact time of about 90 minutes. The wt. % of phenol removal is based on the total weight of phenols in the stream.

It will be noted that because the activity of some metals is greater than that of other metals under a given set of conditions, less of the more active metal, for a given amount of phenols in the feed stream is required to remove a predetermined amount of the phenols from the stream. For example, at a temperature of 25° C. and a contact time of 90 minutes, 17 wt. % of phenols are removed from a phenol-containing coal liquid using zinc hydroxide at a metal to oxygen mol ratio of 1.0 whereas at the same temperature and metal to oxygen mol ratio, about 72 wt. % of phenols are removed from the same coal liquid when calcium hydroxide is used. The relative activity of one metal to another is known in the art and the ratio of any given metal to oxygen can be determined by either routine experimentation or calculation by one having ordinary skill in the art.

In order to achieve a high percentage of phenol removal with any metal, a multistage process can be used. For example, at a calcium to oxygen mol ratio of 0.2, a contact time of 90 minutes, and at a temperature of 25° C., 48 wt. % removal of phenols from a coal liquid is achieved. If the treated coal liquid is contacted a second time under the same mol ratio, time, and temperature conditions as the first stage, an overall 77 wt. % removal of phenols is achieved. Therefore, it may be desirable to contact the liquid from a previous stage many times over to effect substantially total removal of the phenols from the stream. For example, after initial contact of the stream with the multivalent metal composition, the treated stream is separated from the resulting hydroxy metal phenate and passed on to another stage for contact with additional multivalent metal composition. This sequence can be repeated as often as practical and desirable.

It may be desirable from an energy savings point of view that the phenol-containing hydrocarbonaceous stream be at elevated temperatures when contacted with the multivalent metal composition. In this context, elevated temperatures means temperatures greater than room temperature but lower than the decomposition temperature of the resulting hydroxy metal phenate. Generally, the phenol-containing feed stream will result from a chemical, petroleum or coal process and will exit such process at elevated temperatures whereupon it can be treated directly with the multivalent metal composition as long as the temperature of the stream is lower than the decomposition temperature of the resulting hydroxy metal phenate. Therefore, the temperature of the phenol-containing feed stream is dependent on the source and process for its production and may have to be cooled to a lower temperature before treatment.

Preferably it is desirable to treat the feed stream with the multivalent metal composition as close to the decomposition temperature of the resulting hydroxy metal phenate as possible. By doing so, the rate of reaction is increased and the addition of heat is not required to bring the feed stream up to an efficient reaction temperature. Therefore, if the feed stream exits a previous process already at elevated temperatures, and is treated according to the invention at those temperatures, an energy savings is realized because no external heat is needed for elevating the temperature of the feed stream to a more desirable reaction temperature.

Although not wishing to be limited by theory, it is believed that the multivalent metals suitable for use herein form a hydroxy metal phenate with the phenol compounds contained in the hydrocarbonaceous stream. These hydroxy metal phenates can undergo intramolecular protron transfer. For example, if calcium hydroxide were used as the multivalent metal composition to remove phenols according to the present invention, it is believed the following hydroxy metal phenate and reaction would result:

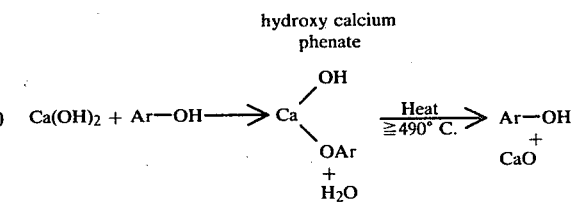

where Ar-OH represents a phenol compound or phenolic functionality in the hydrocarbonaceous stream. As shown above, upon heating the hydroxy metal phenate to its decomposition temperature, the phenol compound is regenerated and an oxide of the multivalent metal is produced. This oxide can be hydrolyzed to form the corresponding hydroxide and recycled in a continuous process or it can be recycled directly as the oxide if so desired.

In contrast to the above, if a monovalent metal composition such as sodium or potassium oxide or hydroxide is used for removal of phenols from a phenol-containing stream, the following salt and reaction would result:

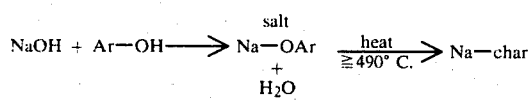

The above reaction shows that a monovalent metal composition, or even some multivalent metal compositions, would form a salt other than a hydroxy metal phenate and would be incapable of regenerating the phenols and an metal oxide when heated to its decomposition temperature.

It will be noted that, if present, carboxylic compositions may also be removed from the hydrocarbonaceous stream when treated according to the present invention.

A preferred method of practicing the present invention is a continuous stirred tank reactor process which comprises contacting a phenol-containing hydrocarbonaceous feed stream with a predetermined concentration of multivalent metal oxide, and/or hydroxide composition. This multivalent metal composition can contact the hydrocarbonaceous stream as either a solid or as an aqueous slurry containing the solid multivalent metal composition. It is preferred that the hydrocarbonaceous stream be contacted with only solid particles of the multivalent metal composition so as to eliminate an aqueous phase.

As previously discussed, the amount of multivalent metal composition contacting the stream is dependent on the desired mol ratio of metal to phenolic-oxygen in the stream. For purposes of this invention, it is preferred that the mol ratio be at least that which will remove at least 15 wt. % of phenols from the stream. The multivalent metal composition and stream are preferably slurried to assure contact of the phenols with the multivalent metal composition. The phenols in the stream react with the multivalent metal composition thereby forming a hydroxy metal phenate. The hydroxy metal phenate is separated from the stream by any conventional method and the hydrocarbonaceous effluent portion of the stream is passed on for further processing, further contacting with additional multivalent metal compositions, or such treatment as hydrofining. The hydroxy metal phenate is removed and dried and any residual portions still containing phenolic functionality can be recycled to the feed stream. The dried hydroxy metal phenate is heated to its decomposition temperature thereby generating phenols as well as oxides of the multivalent metal(s). The phenols are collected and the metal oxides are either recycled directly to the hydrocarbonaceous feed stream or they are first hydrolyzed by any conventional means, preferably by the introduction to the stream of stoichiometric amounts of water, to convert the oxides to their corresponding preferred hydroxides. These hydroxides are then recycled and contacted with the feed stream. Of course, multistage processing can be performed until the desired level of phenol removal is achieved.

Other methods which can be used in practicing the present invention are fluidized or fixed bed processes using phenol sorbent materials. Suitable phenol sorbent materials include basic ceramic sorbents such as barium titanate, calcium titanate, calcium aluminate cement, and the like.

Other conventional solid/fluid processes can also be used. Non-limiting examples of such other processes include cyclic fluid bed, tube flow reactor and moving bed processes.

The presence of the hydroxy metal phenate which is formed during the practice of this invention is supported by conventional elemental analysis. That is, the amount of carbon, hydrogen and metal for each hydroxyl metal phenate can be calculated empirically then substantiated by elemental analysis data.

The following examples serve to more fully describe the present invention. It is understood that these examples in no way serve to limit the true scope of this invention, but rather, are presented for illustrative purposes.

EXAMPLES 1–4

Various multivalent metal oxides were used to extract phenols from a phenol-containing naphtha cut derived from a coal liquefaction process. The naphtha cut contained 1 mmol of oxygen/gm of naphtha, which oxygen is essentially all present as phenols. Concentrations of oxides were used to give a mol ratio of metal in the oxide to phenolic-oxygen in the naphtha cut of 1.0. The naphtha cut in each instance was contacted for 90 minutes with the multivalent metal oxide at a temperature of 25° C. A hydroxy metal phenate resulted and was separated from the treated naphtha cut. The amount of phenols removed was determined by gas chromatography wherein the phenol content of the non-treated naphtha was compared to that of the treated naphtha. The results are set forth in Table I below

TABLE I

Effect of Metal Atom on Removal of Phenols When Used in Oxide Form

| Ex | Metal Ion | Wt. % Phenol Removal |
|---|---|---|
| 1 | $Ca^{++}$ | 49 |
| 2 | $Sr^{++}$ | 65 |
| 3 | $Ba^{++}$ | 100 |
| 4 | $Ni^{+++}$ | 25 |

The above table shows that at a mol ratio of metal to phenolic-oxygen of 1, at a temperature of 25° C. and for a contact time of 90 minutes, the oxides of Ca, Sr, Ba and $Ni^{3+}$ are able to remove at least 25 wt. % of the phenols from the phenol-containing naphtha stream. The weight percent of phenol removed is based on the total weight of phenols in the untreated naphtha stream.

COMPARATIVE EXAMPLES A–D

For comparative purposes, various multivalent metal oxides, other than those of Examples 1–4, were used according to the conditions set forth in Examples 1–4. The results are shown in Table II below

TABLE II

Effect of Metal Atom on Removal of Phenol When Used in Oxide Form

| Ex | Metal Ion | Wt. % of Phenol Removal |
|---|---|---|
| A | $Mg^{++}$ | 5 |
| B | $Zn^{++}$ | 9.8 |
| C | $Ni^{++}$ | 9 |

TABLE II-continued

Effect of Metal Atom on Removal of Phenol When Used in Oxide Form

| Ex | Metal Ion | Wt. % of Phenol Removal |
|---|---|---|
| D | $Ce^{4+}$ | 3 |

The above table shows that not all multivalent metal oxides are capable of removing at least 15 wt. % of phenols from the untreated naphtha cut.

EXAMPLES 5-10

Various multivalent metal oxides were used to remove phenols from the same naphtha cut and under the same conditions set forth in Examples 1-4 except, a stoichiometric amount of water was added to completely (hydrate) convert the metal oxide to the corresponding hydroxide. The results are set forth in Table III below.

TABLE III

Effect of Metal Atom on Removal of Phenols When Used in Hydroxide Form

| Ex | Metal Ion | Wt. % Phenol Removal |
|---|---|---|
| 5 | $Ca^{++}$ | 72 |
| 6 | $Sr^{++}$ | 99 |
| 7 | $Ba^{++}$ | 100 |
| 8 | $Zn^{++}$ | 17 |
| 9 | $Ni^{++}$ | 15 |
| 10 | $Ni^{+++}$ | 53 |

Table III shows, that generally, the multivalent metal hydroxide is preferred over the corresponding oxide because of its increased phenol removal capabilities. Although when barium is the multivalent metal, substantially all of the phenols are removed with either the oxide or hydroxide form.

COMPARATIVE EXAMPLE E

Comparative example D was repeated except a stoichiometric amount of water was added to completely (hydrate) convert cerium oxide to cerium hydroxide during phenol removal. After analysis by gas chromatography, it was found that the amount of phenol removal for cerium hydroxide was 7 wt. % vs. 3 wt. % for the corresponding oxide. This shows that even the hydroxide form of some multivalent metals is incapable of removing at least 15 wt. % of the phenols from a phenol-containing naphtha stream.

EXAMPLES 11-18

Various mol ratios of calcium, in its hydroxide form, to oxygen, in the naphtha cut, were used to remove phenols from the naphtha stream of Examples 1-4. These runs were performed at 25° C. for a 90 minute contact time in either 1 or 2 stage processes as indicated below. That is, if the process was a two stage process, the naphtha stream (treated or untreated depending on the stage) was contacted with calcium hydroxide for 90 minutes in each stage. The results are set forth in Table IV below.

TABLE IV

Comparison of Removal Efficiencies for 1 and 2 Stage Batch Processes at Various M/O Values

| Ex | M/O Ratio | # of Stages | Wt. % of Phenol Removal[a] |
|---|---|---|---|
| 11 | 0.1 | 1 | 32 |
| 12 | 0.1 | 2 | 54 |
| 13 | 0.2 | 1 | 48 |
| 14 | 0.2 | 2 | 77 |
| 15 | 0.4 | 1 | 61 |
| 16 | 0.4 | 2 | 81 |
| 17 | 0.8 | 1 | 70 |
| 18 | 0.8 | 2 | — |

This table shows the advantage of using more than one stage for removal of phenols from a phenol-containing naphtha stream. For example, a two stage process using a specific M/O value for each stage is capable of removing more of the phenols that a one stage process using an M/O value double that of the corresponding two stage process under the same conditions.

EXAMPLES 19-21

Samples of hydroxy calcium phenate were pyrolyzed under a nitrogen sweep at various temperatures, and residence times in a pyrolyzer. The products from the pyrolysis were analyzed by gas chromatography and the results are illustrated in Table V below.

TABLE V

Pyrolysis of Hydroxy Calcium Phenate

| Ex. | Temp. °C. | Residence Time (min) | % Liquid | % Solid | Analysis of Liquid by GC % Phenol |
|---|---|---|---|---|---|
| 19 | 550 | 5 | 24±2 | 77±1 | 97±2 |
| 20 | 650 | 5 | 39±2 | 60±2 | 94±1 |
| 21 | 650 | 60 | 60±3 | 40±2 | 97±1 |

The above table illustrates that upon pyrolysis, hydroxy calcium phenate decomposed to form a liquid which was found to consist substantially of phenol. The solid in example 21 was found to contain more than 95 wt. % calcium oxide.

EXAMPLES 22-23

Samples of hydroxy calcium p-cresylate were pyrolyzed under a nitrogen sweep at various temperatures and residence times in a pyrolyzer. The products were analyzed by gas chromatography and results are illustrated in Table VI below.

TABLE VI

Pyrolysis of Hydroxy Calcium p-methyl phenate

| Ex. | Temp. 20°C. | Residence Time (min) | % Liquid | % Solid | % Gas | % Phenol | % Cresols |
|---|---|---|---|---|---|---|---|
| 22 | 550 | 5 | 8 | 92 | — | — | 798 |
| 23 | 650 | 5 | 35±3 | 61±1 | 4±3[a] | 24±1 | 38±3 |

[a]analysis of gas indicated approximately 80% methane and approximately 10% hydrogen.

EXAMPLE 24

100 grams coal naphtha (from EDS liquefaction process using Illinois No. 6 coal and containing about 8.8 wt. % phenols), 10 grams $Ca(OH)_2$ and 40 grams $H_2O$ were stirred under $N_2$ at 85°-86° C. for 3 hours. The product mixture was cooled and washed with 130 ml of 25% isopropranol/water. After separating the oil layer, the solids in the aqueous layer were separated by decantation and dried at 60° C. (1 mm Hg) for 30 minutes.

The separated oil was analyzed by gas chromatography and showed a 96 wt% phenol removal and a 78 wt% cresol removal.

Pyrolysis of the dried salt at 650° C. for 5 minutes under $N_2$ gave a liquid condensate which contained 54% phenol and 46% cresols by gas chromatographic analysis. The solid residue consisted of calcium oxide and unreacted hydroxy calcium phenates.

What is claimed is:

1. A process for removing phenols from a phenol-containing coal liquid and regenerating the phenols, the process comprising:
   (a) containing the coal liquid with a multivalent metal composition selected from the group consisting of oxides and/or hydroxides of one or more multivalent metals capable of forming a hydroxy metal phenate with the phenols of the stream, wherein said contacting is performed at temperatures lower than the decomposition temperature of the hydroxy metal phenate;
   (b) separating the hydroxy metal phenate from the treated stream; and
   (c) heating the hydroxy metal phenate to its decomposition temperature, thereby forming phenols and oxides of the multivalent metal.

2. The process of claim 1 wherein the mol ratio of multivalent metal to phenolic oxygen in the stream is such that at least 15 wt. % of the phenols are removed from the stream.

3. The process of claim 1 wherein the multivalent metal is selected from the group consisting of Ca, Ba, Sr and $Ni^{+++}$.

4. The process of claim 2 wherein the multivalent metal is selected from the group consisting of Ca, Ba, Sr and $Ni^{+++}$.

5. The process of claim 4 wherein the multivalent metal composition is a hydroxide.

6. The process of claim 5 wherein the multivalent metal composition is calcium hydroxide.

7. The process of claim 1 wherein the process is continuous and the resulting multivalent metal oxides are recycled to the coal liquid.

8. The process of claim 7 wherein the multivalent metal oxides are first hydrolyzed to the corresponding hydroxides before being recycled to the coal liquid.

9. The process of claim 1 wherein the stream contains a stoichiometric amount of water to hydrolyze any multivalent oxides to hydroxides.

10. A process for removing phenols from a phenol-containing hydrocarbonaceous stream and regenerating the phenols, the process comprising:
    (a) contacting the stream with a multivalent metal composition selected from the group consisting of oxides and/or hydroxides of one or more multivalent metals capable of forming a hydroxy metal phenate with the phenols of the stream, wherein said contacting is performed at temperatures lower than the decomposition temperature of the hydroxy metal phenate;
    (b) separating the hydroxy metal phenate from the treated stream; and
    (c) heating the hydroxy metal phenate to its decomposition temperature, thereby forming phenols and oxides of the multivalent metal.

11. The process of claim 10 wherein the mol ratio of multivalent metal to phenolic oxygen in the stream is such that at least 15 wt. % of the phenols are removed from the stream.

12. The process of claim 10 wherein the multivalent metal is selected from the group consisting of Ca, Ba, Sr and $Ni^{+++}$.

13. The process of claim 11 wherein the multivalent metal is selected from the group consisting of Ca, Ba, Sr and $Ni^{+++}$.

14. The process of claim 13 wherein the multivalent metal composition is a hydroxide.

15. The process of claim 14 wherein the multivalent metal composition is calcium hydroxide.

16. The process of claim 10 wherein the process is continuous and the resulting multivalent metal oxides are recycled to the hydrocarbonaceous stream.

17. The process of claim 16 wherein the multivalent metal oxides are first hydrolyzed to the corresponding hydroxides before being recycled to the hydrocarbonaceous stream.

18. The process of claim 10 wherein the stream contains a stoichiometric amount of water to hydrolyze any multivalent oxides to hydroxides.

* * * * *